(12) United States Patent
Okada et al.

(10) Patent No.: US 9,017,267 B2
(45) Date of Patent: Apr. 28, 2015

(54) INTERSTITIAL FLUID COLLECTION METHOD AND INTERSTITIAL FLUID COLLECTION KIT AND INTERSTITIAL FLUID COLLECTION SHEET USED FOR THE METHOD

(75) Inventors: Seiki Okada, Kobe (JP); Yoshihiro Asakura, Kobe (JP); Akihito Takezaki, Bunkyo-ku (JP); Kazuki Isobe, Bunkyo-ku (JP)

(73) Assignee: Sysmex Corporation, Hyogo (JP)

( * ) Notice: Subject to any disclaimer, the term of this patent is extended or adjusted under 35 U.S.C. 154(b) by 772 days.

(21) Appl. No.: 12/883,824

(22) Filed: Sep. 16, 2010

(65) Prior Publication Data

US 2011/0066076 A1    Mar. 17, 2011

(30) Foreign Application Priority Data

Sep. 16, 2009 (JP) ................................. 2009-214633

(51) Int. Cl.
| | |
|---|---|
| *A61B 5/15* | (2006.01) |
| *A61B 10/00* | (2006.01) |
| *A61B 5/145* | (2006.01) |
| *A61B 5/1455* | (2006.01) |
| *A61B 5/1477* | (2006.01) |

(52) U.S. Cl.
CPC ......... *A61B 10/0045* (2013.01); *A61B 5/14514* (2013.01); *A61B 5/14532* (2013.01); *A61B 5/14546* (2013.01); *A61B 5/1455* (2013.01); *A61B 5/1477* (2013.01); *A61B 2010/008* (2013.01)

(58) Field of Classification Search
CPC .. A61B 5/145; A61B 5/14507; A61B 5/1451; A61B 5/14514

USPC .................................. 600/573, 575, 580, 584
See application file for complete search history.

(56) References Cited

U.S. PATENT DOCUMENTS

| | | | | |
|---|---|---|---|---|
| 4,759,968 A | * | 7/1988 | Janssen | 428/202 |
| 5,000,172 A | | 3/1991 | Ward | |
| RE33,727 E | * | 10/1991 | Sims | 128/851 |
| 5,749,842 A | | 5/1998 | Cheong | |
| 6,063,029 A | * | 5/2000 | Saita et al. | 600/309 |
| 2003/0100846 A1 | | 5/2003 | Custer et al. | |
| 2003/0113827 A1 | * | 6/2003 | Burkoth | 435/14 |
| 2003/0180493 A1 | * | 9/2003 | Hirashima et al. | 428/40.1 |
| 2005/0177037 A1 | * | 8/2005 | Okada et al. | 600/347 |
| 2006/0094945 A1 | | 5/2006 | Barman | |

FOREIGN PATENT DOCUMENTS

| | | |
|---|---|---|
| JP | 2-23965 | 1/1990 |
| JP | 7-148198 | 6/1995 |
| JP | 2005-513428 A | 5/2005 |
| JP | 2005-218855 | 8/2005 |
| JP | 2007-236844 A | 9/2007 |
| JP | 2008-518662 | 6/2008 |
| WO | 00/74767 A2 | 12/2000 |
| WO | 01/43643 A1 | 2/2001 |
| WO | 02/02177 A1 | 1/2002 |
| WO | 03/052125 A1 | 6/2003 |

* cited by examiner

*Primary Examiner* — Max Hindenburg
*Assistant Examiner* — John Pani
(74) *Attorney, Agent, or Firm* — Sughrue Mion, PLLC

(57) ABSTRACT

A interstitial fluid collection kit for collecting interstitial fluid extracted via micropores formed in a skin is disclosed. The kit includes a marker sheet that has an adhesive face and that defines a region in which micropores are to be formed; a transparent retention sheet having an adhesive face; and a collecting body that is retained by a part of the adhesive face of the retention sheet and that collects interstitial fluid extracted from the skin.

10 Claims, 15 Drawing Sheets (a)

(b)

(a)

(b)

INTERSTITIAL FLUID COLLECTION METHOD AND INTERSTITIAL FLUID COLLECTION KIT AND INTERSTITIAL FLUID COLLECTION SHEET USED FOR THE METHOD

TECHNICAL FIELD

The present invention relates to a method of collecting interstitial fluid extracted from micropores formed in skin of a living body, and a interstitial fluid collection kit and a interstitial fluid collection sheet used for the method.

BACKGROUND ART

Conventionally, there has been known a method of forming micropores in a skin of a living body to thereby collect living body components via the micropores for measurement (see Patent Literatures 1 and 2 for example).

Patent Literature 1 discloses a method according to which particles are caused to collide with skin to form micropaths in the skin after which an occlusive dressing including gel for collecting analyte is attached to a processing region including the micropaths, to thereby collect the analyte in the gel via the micropath.

Patent Literature 2 discloses a blood glucose value analysis apparatus that includes: a main body to which an extraction cartridge for collecting interstitial fluid can be attached; a receiving section for the positioning of a puncture tool for forming micropores in the skin; and a belt section for attaching the receiving section to an arm of a user.

The receiving section in Patent Literature 2 has an opening for exposing the skin of the user. This receiving section is configured so that the processing region of the skin including the micropores formed by the puncture tool is exposed through the opening. The main body is rotatably attached by a hinge to the receiving section. The main body is configured so that the main body is rotated to the receiving section to allow the extraction cartridge attached to the main body is placed on the processing region of the skin, thus providing the positioning of the extraction cartridge to the processing region of the skin. Then, while the receiving section being attached to the arm by the belt section, the extraction of interstitial fluid is carried out by the extraction cartridge.

CITATION LIST

Patent Literature

Patent Literature 1: Published Japanese translation of a PCT application No. 2005-513428
Patent Literature 2: Japanese Unexamined Patent Publication No. 2007-236844

SUMMARY OF INVENTION

Technical Problem

In order to perform an accurate extraction of interstitial fluid, it is required to correctly position a medium for extracting the interstitial fluid at the region of the skin including the micropores. However, Patent Literature 1 does not disclose any positioning of an occlusive dressing to the processing region.

On the other hand, according to the apparatus disclosed in Patent Literature 2, the main body attached with the extraction cartridge is configured to be rotatable to the receiving section having the opening through which the processing region is exposed, to thereby provide the positioning of the extraction cartridge at the processing region. However, this configuration requires the receiving section to be attached to the arm by the belt section during extraction of interstitial fluid. Thus, if interstitial fluid must be extracted for a long time, the belt must be kept attached to the arm.

The present invention has been made in view of the situation as described above. It is an objective of the present invention to provide an interstitial fluid collection method and an interstitial fluid collection kit and an interstitial fluid collection sheet used for the method by which a medium for extracting interstitial fluid can be easily positioned, without causing a burden on a user, on a processing region of a skin.

Solution to the Problem

A interstitial fluid collection method according to a first aspect of the present invention (hereinafter also simply referred to as "method") is characterized in including:
  a step of adhering, to skin, a marker sheet that has an adhesive face and that defines a region in which micropores are to be formed;
  a step of forming micropores in the region defined by the marker sheet adhered to the skin;
  a step of adhering an interstitial fluid collection sheet to the skin by an adhesive face of a retention sheet by using the marker sheet adhered to the skin as a marker so that a collecting body is placed on the region in which micropores are to be formed, the interstitial fluid collection sheet including a transparent retention sheet having an adhesive face, and a collecting body that is retained by a part of the adhesive face of the retention sheet and that collects interstitial fluid extracted from the skin; and
  a step of collecting interstitial fluid from the skin via the micropores to the collecting body.

According to the method of the present invention, the marker sheet adhered to the skin defines a micropore formation region. Furthermore, the retention sheet that retains the collecting body for collecting interstitial fluid is transparent. Thus, by using the marker sheet as a marker, the collecting body can be easily placed in the micropore formation region. Interstitial fluid can be extracted only by adhering the sheets (marker sheet, interstitial fluid collection sheet) to the skin. Thus, even if interstitial fluid is extracted for a long time, it is not necessary to keep attaching an aid such as a belt to the arm, so that the burden to the user is reduced.

The collecting body is retained by a part of the adhesive face of the retention sheet. Due to a manufacture reason, there may be a variation in the position of the collecting body in the adhesive face. In such a case, the position at which the collecting body is adhered undesirably varies even when the interstitial fluid collection sheet is adhered to a predetermined region of the skin based on the outer shape of the interstitial fluid collection sheet. However, according to the present invention, since the retention sheet is transparent, even when the position of the collecting body in the retention sheet varies, the interstitial fluid collection sheet can be adhered to the skin, while visually recognizing the position of the collecting body, so that the collecting body is positioned within the region defined by the marker sheet. This consequently allows, regardless of the variation of the position of the collecting body in the retention sheet, the collecting body to be placed in the micropore formation region.

The term "transparent" herein means to include colorless transparent and colored transparent. The term "transparent" is not limited to completely-transparent and means to include "translucent" so long as such transparency is obtained that allows the position of the collecting body to be confirmed via the retention sheet. For example, the term "transparent" herein also includes a configuration where the part at which the collecting body is retained and the periphery thereof of a few millimeters are transparent and the other parts are not transparent. The term "transparent" herein also includes a configuration where a grid-like pattern is given to the retention sheet and the patterned part is not transparent, so long as the position of the collecting body can be confirmed through transparent parts other than the pattern.

A interstitial fluid collection kit according to the second aspect of the present invention is a interstitial fluid collection kit for collecting interstitial fluid extracted via micropores formed in a skin, characterized in comprising:
 a marker sheet that has an adhesive face and that defines a region in which micropores are to be formed;
 a transparent retention sheet having an adhesive face; and
 a collecting body that is retained by a part of the adhesive face of the retention sheet and that collects interstitial fluid extracted from the skin.

As in the above-mentioned method, a interstitial fluid collection sheet of the present invention is configured so that the marker sheet adhered to the skin defines a micropore formation region. Furthermore, the retention sheet for retaining the collecting body for collecting interstitial fluid is transparent. Thus, by using the marker sheet as a marker, the collecting body can be easily placed in the micropore formation region. The interstitial fluid can be extracted only by adhering the sheets (marker sheet, interstitial fluid collection sheet) to the skin. Thus, even if interstitial fluid is extracted for a long time, it is not necessary to keep attaching an aid such as a belt to the arm, so that the burden to the user is reduced.

Furthermore, the collecting body is retained by a part of the adhesive face of the retention sheet. Due to a manufacture reason, there may be a variation in the position of the collecting body in the adhesive face. In such a case, the position at which the collecting body is adhered undesirably varies even when the interstitial fluid collection sheet is adhered to a predetermined region of the skin based on the outer shape of the interstitial fluid collection sheet. However, according to the present invention, since the retention sheet is transparent, even when the position of the collecting body in the retention sheet varies, the interstitial fluid collection sheet can be adhered to the skin, while visually recognizing the position of the collecting body, so that the collecting body is positioned within the region defined by the marker sheet. This consequently allows, regardless of the variation of the position of the collecting body in the retention sheet, the collecting body to be placed in the micropore formation region.

Furthermore, in the interstitial fluid collection kit, the marker sheet is preferably a frame-like sheet having an opening that defines the region.

Furthermore, in the interstitial fluid collection kit, the marker sheet preferably consists of a plurality of small pieces by which the region is defined.

Furthermore, in the interstitial fluid collection kit, the collecting body is preferably gel. In this case, the gel is preferably colored.

Furthermore, in the interstitial fluid collection kit, the collecting body is preferably smaller than the opening of the marker sheet.

Furthermore, in the interstitial fluid collection kit, the marker sheet is preferably colored.

Furthermore, in the interstitial fluid collection kit, the marker sheet preferably has a positioning mark corresponding to a positioning mark provided on a flange provided at a side at which a micropore formation tool for forming micropores is abbutable to the skin.

Furthermore, it is preferable that the interstitial fluid collection kit further comprises a marker retention sheet that has a first adhesive face adhered to a back face of the adhesive face of the marker sheet by a first adhesive that retains the marker sheet to the first adhesive face, and the adhesive face of the marker sheet has a second adhesive having a strength higher than the strength of the first adhesive. In this case, the marker retention sheet preferably has a positioning mark corresponding to a positioning mark provided on a flange provided at a side on which a micropore formation tool for forming micropores is abuttable to the skin.

Furthermore, in the interstitial fluid collection kit, the adhesive face of the retention sheet is preferably adhered to the back face of the adhesive face of the marker sheet with a lower adhesive strength than the adhesive strength of the marker sheet to the skin.

Furthermore, a interstitial fluid collection sheet according to the third aspect of the present invention is a interstitial fluid collection sheet for collecting interstitial fluid extracted via micropores formed in a region defined by a marker sheet adherable to skin, comprising:
 a transparent retention sheet having an adhesive face; and
 a collecting body that is retained by a part of the adhesive face of the retention sheet and that is capable of collecting extracted interstitial fluid.

Furthermore, in the interstitial fluid collection sheet, the adhesive face of the retention sheet is preferably adhered to a back face of the adhesive face of the marker sheet with an adhesive strength lower than an adhesive strength of the marker sheet to skin.

Furthermore, in the interstitial fluid collection sheet, the collecting body is preferably gel.

Furthermore, in the interstitial fluid collection sheet, it is preferable that the gel itself is colored or a colored intermediate layer is used.

Advantageous Effects of Invention

According to an interstitial fluid collection method and an interstitial fluid collection kit and an interstitial fluid collection sheet used for the method of the present invention, a medium for extracting interstitial fluid can be positioned in a processing region of the skin without causing a burden to a user.

DESCRIPTION OF EMBODIMENTS

The following section will describe in detail, with reference to the attached drawings, an interstitial fluid collection method and an interstitial fluid collection kit and an interstitial fluid collection sheet used for the method in the present embodiment.

The method for example in the present embodiment relates to a technique of collecting interstitial fluid from micropores formed in skin. First, the following section will describe a puncture tool for forming such micropores.

[Puncture Tool]

Figure 1:
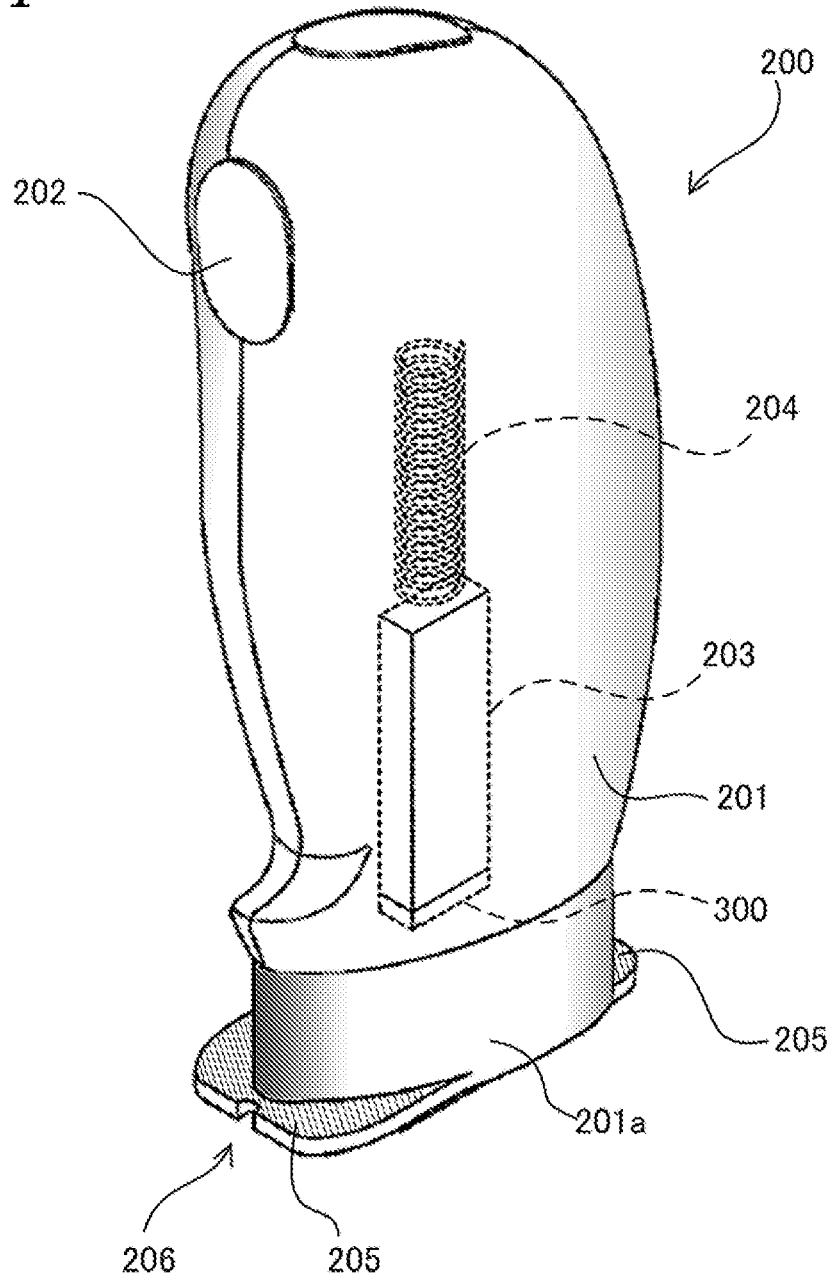
FIG. 1 is a perspective illustration diagram of an example of a puncture tool used in a interstitial fluid collection method of the present embodiment.
Figure 2:
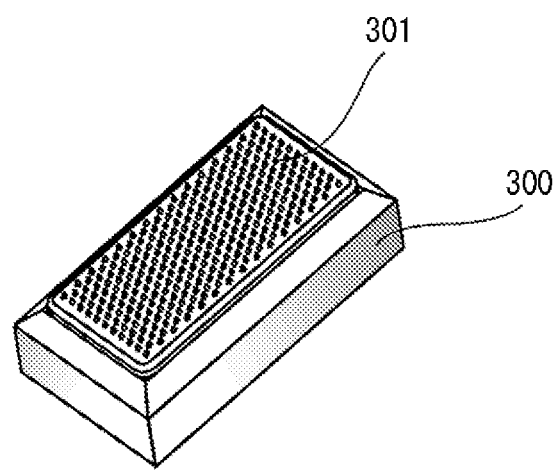
FIG. 2 is a perspective view of a fine needle chip attached to the puncture tool shown in FIG. 1.
Figure 3:
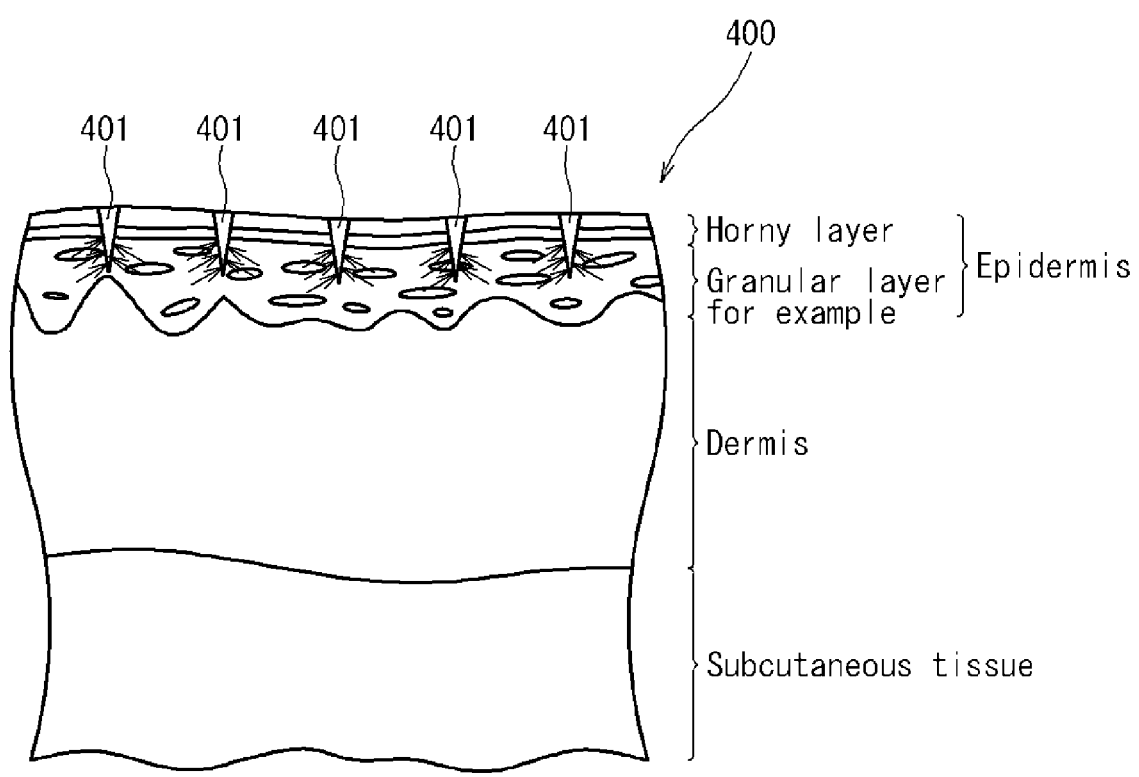
FIG. 3 is a cross-sectional illustration diagram of skin in which micropores are formed by the puncture tool.

FIG. 1 is a perspective illustration diagram of an example of a puncture tool 200 used for the interstitial fluid collection method of the present embodiment. FIG. 2 is a perspective view of a fine needle chip 300 attached to the puncture tool 200 shown in FIG. 1. FIG. 3 is a cross-sectional illustration diagram of a skin in which micropores are formed by the puncture tool 200.

As shown in FIGS. 1 to 3, the puncture tool 200 is a device that is used in the following manner. Specifically, the puncture tool 200 is attached with the fine needle chip 300 subjected to a sterilization processing and fine needles 301 of the fine needle chip 300 are abutted to the epidermis of a living body (skin 400 of a subject) to thereby form interstitial fluid extraction holes (micropores 401) in the skin 400 of the subject. The fine needle 301 of the fine needle chip 300 is sized so that, when the micropores 401 are formed by the puncture tool 200, the micropores 401 are held within the epidermis of the skin 400 and are prevented from reaching the dermis.

As shown in FIG. 1, the puncture tool 200 comprises a housing 201, a release button 202 provided at the surface of the housing 201, and an array chuck 203 and a spring member 204 both of which being provided in the housing 201. A lower end face (a face abutable to skin) of a lower section 201a of the housing 201 includes an opening (not shown) through which the fine needle chip 300 can pass. The spring member 204 has a function to bias the array chuck 203 in a puncture direction. The lower end of the array chuck 203 can be attached with the fine needle chip 300. The lower face of the fine needle chip 300 includes a plurality of fine needles 301. The fine needle chip 300 has a lower face having a size of 10 mm (long side)×5 mm (short side). The puncture tool 200 has a fixing mechanism (not shown) that fixes the array chuck 203 against the biasing force of the spring member 204 while the array chuck 203 being pushed in an upward direction (anti-puncture direction). When a user (subject) depresses the release button 202, the fixing of the array chuck 203 by the fixing mechanism is released. Then, the biasing force by the spring member 204 causes the array chuck 203 to move in the puncture direction. Then, the fine needles 301 of the fine needle chip 300 protruding through the opening puncture the skin.

The housing 201 includes a flange 205 as shown by diagonal lines in FIG. 1. The flange 205 includes a notch 206 as a positioning mark (which will be described later). Although only one notch is shown in FIG. 1, the flange 205 at the back side of FIG. 1 also includes the same notch 206 as that shown at the front side.

[Interstitial Fluid Collection Kit]

Next, a interstitial fluid collection kit will be described. The interstitial fluid collection kit is used to collect interstitial fluid extracted through micropores formed in the skin using the puncture tool as described above. The interstitial fluid collection kit comprises: a marker sheet; a marker retention sheet for retaining the marker sheet; a collecting body for collecting interstitial fluid extracted from the skin; and a retention sheet for retaining the collecting body. The following section will describe the respective elements.

Figure 4:
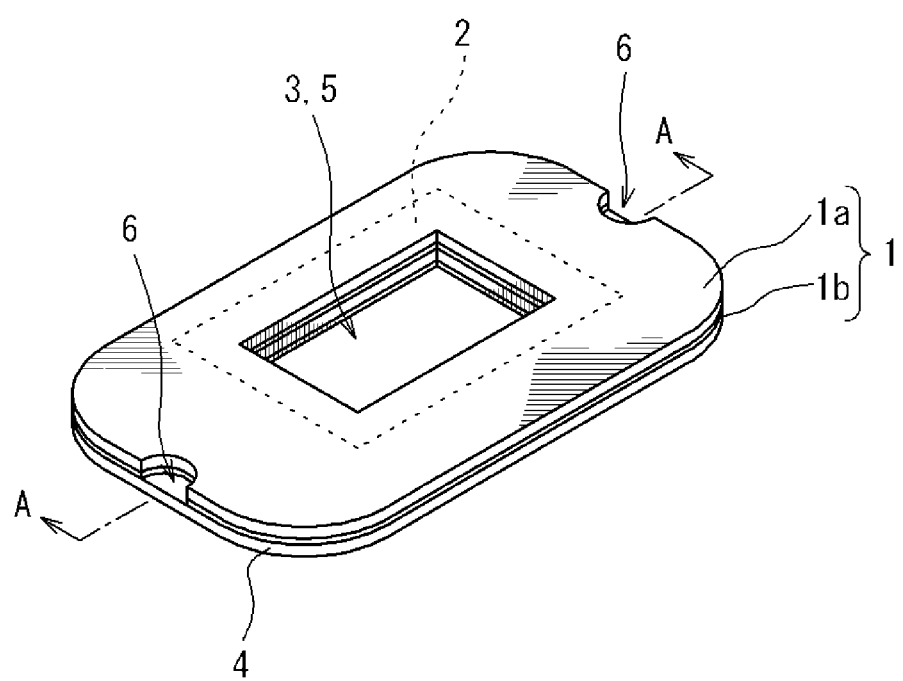
FIG. 4 is a perspective illustration diagram of a marker sheet retained by a marker retention sheet.
Figure 5:
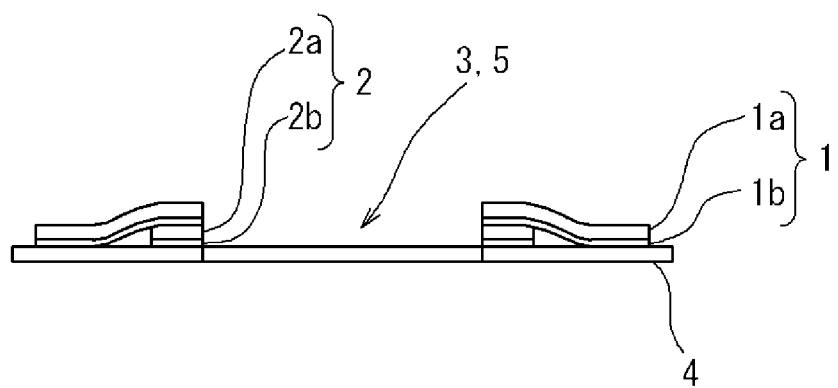
FIG. 5 is a cross-sectional diagram taken along the line A-A of FIG. 4.
Figure 6:
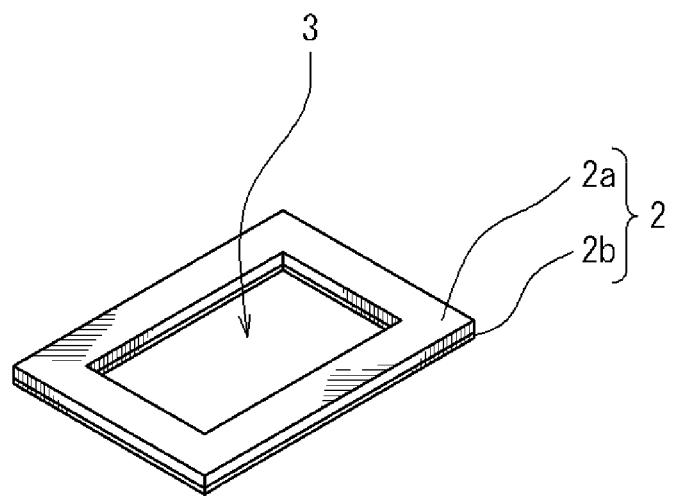
FIG. 6 is a perspective illustration diagram of the marker sheet.

FIG. 4 is a perspective illustration diagram of a marker sheet 2 retained by a marker retention sheet 1. FIG. 5 is a cross-sectional diagram taken along the line A-A of FIG. 4. FIG. 6 is a perspective illustration diagram of the marker sheet. In FIGS. 4 to 6, and FIGS. 7 to 9 which will be described later, for providing easy understanding, the thickness of the sheet for example is drawn exaggeratingly.

The marker sheet 2 is composed of: a sheet body 2a; and an pressure sensitive adhesive layer 2b formed on one face of the sheet body 2a. A face on which the pressure sensitive adhesive layer 2b is formed functions as an adhesive face. The marker sheet 2 is a frame-like sheet having an opening 3. This opening 3 defines a region in which micropores are formed. Specifically, as described later, the fine needle chip 300 of the puncture tool 200 is abutted in the opening 3 to thereby form micropores. Then, the collecting body is placed in the opening 3 to extract interstitial fluid from the micropores. The sheet body 2a of the marker sheet 2 can be formed, for example, by a polyethylene film, a polypropylene film, a polyester film, and a polyurethane film as well as foam, knitted fabric, woven fabric, and nonwoven fabric. The thickness of the sheet body 2a is not particularly limited and is generally about 0.025 to 0.5 mm. The relative sizes of the marker sheet and the retention sheet can be appropriately changed. However, the marker sheet desirably has a smaller size than that of the retention sheet when the sheet body 2a of the marker sheet is made of foam or a nonwoven fabric for example, and thus the drying of the collecting body during the collection of interstitial fluid is facilitated.

The marker sheet 2 is adhered on an oval-shaped peeling sheet 4 that also functions as a mat board. The marker retention sheet 1, which also has an oval shape, is adhered on the peeling sheet 4 so as to cover the marker sheet 2. The marker retention sheet 1 has an opening 5 that has the same size as that of the opening 3 of the marker sheet 2. The marker retention sheet 1 is adhered on the peeling sheet 4 so that the opening 5 is aligned with the opening 3 of the marker sheet 2. The sheet body 1a of the marker retention sheet 1 is preferably formed by a polyethylene film, a polypropylene film, a polyester film, or a polyurethane film for example and is more preferably formed by a polyethylene film, a polyester film, and a polyurethane film. The sheet body 1a also can be formed by foam, knitted fabric, a woven fabric, and a nonwoven fabric for example in addition to a film. The thickness of the sheet body 1a is not particularly limited and is generally about 0.025 to 2.0 mm. The peeling sheet 4 exemplarily includes a high-quality paper processed by mold release agent such as silicone resin, a paper substrate such as a glassine paper, or a sheet such as a polyester film. The thickness of the peeling sheet 4 is not particularly limited and is generally about 0.025 to 0.5 mm.

As in the marker sheet 2, the marker retention sheet 1 is composed of the sheet body 1a and an pressure sensitive adhesive layer 1b formed on one face of the sheet body 1a. A face on which the pressure sensitive adhesive layer 1b is formed functions as an adhesive face. The periphery of the marker retention sheet 1 includes semicircular notches 6 at positions opposed to sandwich the opening 5. By placing the notches 206 of the flange 205 of the puncture tool 200 so as to exactly match the notches 6, the puncture tool 200 can be placed at a predetermined puncture position.

The pressure sensitive adhesive layer 2b of the marker sheet 2 and the pressure sensitive adhesive layer 1b of the marker retention sheet 1 have adhesive strengths that are respectively adjusted so that the adhesive face of the marker sheet 2 has an adhesive strength (the second adhesive strength) higher than the adhesive strength of the adhesive face of the marker retention sheet 1 (the first adhesive strength). This adjustment can be carried out, for example, by a known method such as by for changing the type of pressure sensitive adhesive, by adjusting the amount of tackifier to be included in pressure sensitive adhesive, or by adjusting the timing when tackifier is included in the pressure sensitive adhesive. The adjustment also can be carried out by processing of an adherend face including, for example, the coating of a surface of the sheet body 2a of the marker sheet 2 abutted to the pressure sensitive adhesive layer 1b of the marker retention sheet 1 or a minute convexoconcave processing of the surface of the sheet body 2a.

As described above, by allowing the adhesive face of the marker sheet 2 to have a higher adhesive strength than that of the marker retention sheet 1, when the marker sheet 2 retained by the marker retention sheet 1 is adhered on the skin and then the marker retention sheet 1 is peeled from the skin, only the adhesion having a lower adhesive strength between the marker retention sheet 1 and the marker sheet 2 is released, thus allowing only the marker sheet 2 to be left on the skin. As a result, the frame-like shaped marker sheet 2 can be adhered on the skin easily.

FIG. 6 is a perspective illustration diagram of the marker sheet 2 adhered to the skin. As described above, the marker sheet 2 has a frame-like shape having the opening 3. The size of the opening 3 differs depending on the size of a collecting body placed within the opening and is generally about 1 to 20 mm×1 to 20 mm and is 8 mm×14 mm in the present embodiment. The opening is sized so as to accommodate a collecting body 12 which will be described later. The marker sheet 2 defines a region in which micropores are formed and functions as a marker for placing the collecting body in the micropore formation region. Thus, the marker sheet 2 is preferably colored with blue, red, or green, for example, so that the color of the marker sheet 2 can be distinct from the color of the skin of the living body. The marker sheet 2 colored in the manner as described above allows the collecting body to be placed within the opening 3 in an easy and accurate manner.

Figure 7:
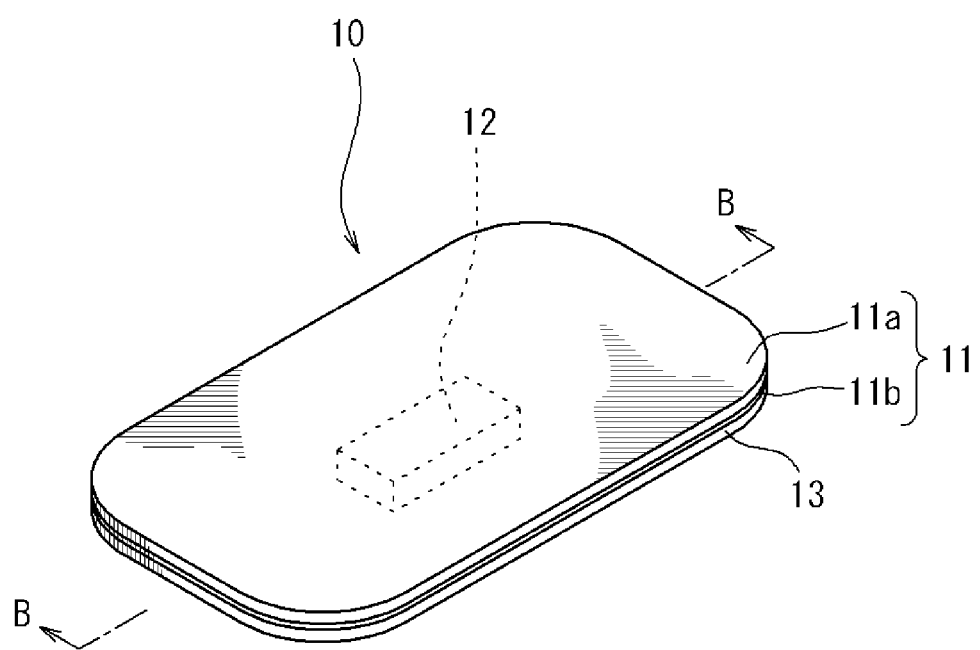
FIG. 7 is a perspective illustration diagram of the interstitial fluid collection sheet.
Figure 8:
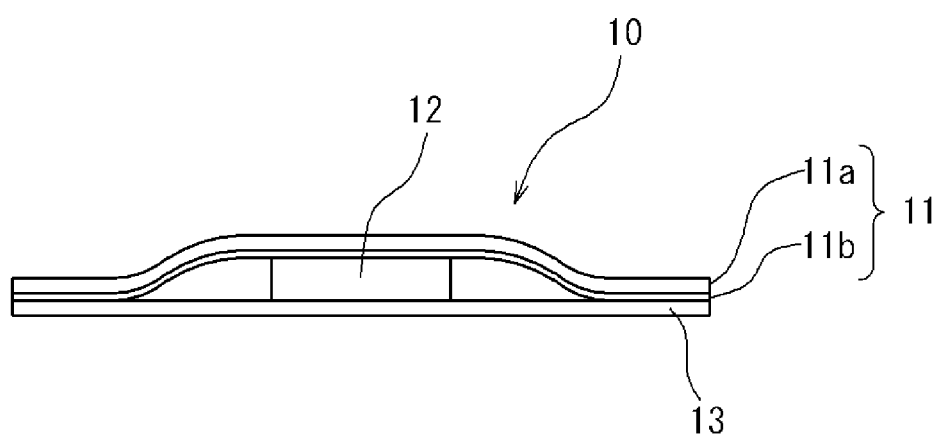
FIG. 8 is a cross-sectional diagram taken along the line B-B of FIG. 7.
Figure 9:
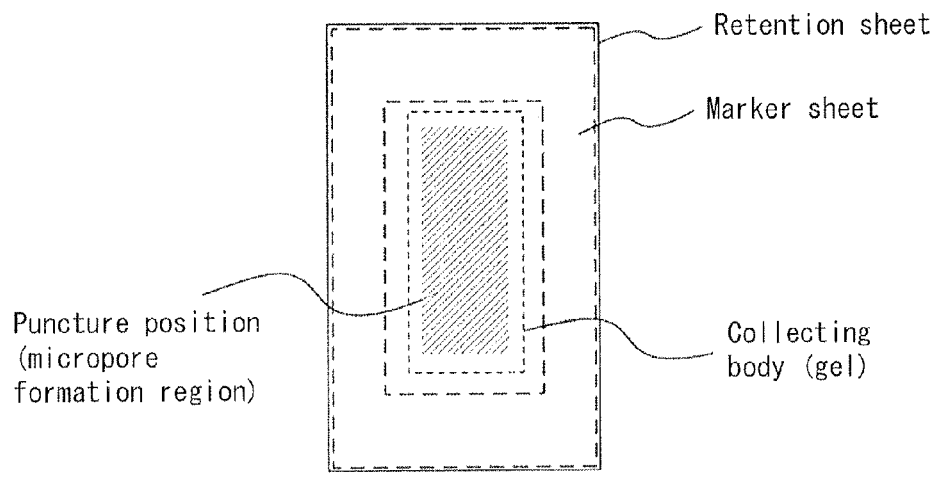
FIGS. 9(a) and 9(b) (Prior Art) are illustration diagrams of a case where an opaque retention sheet is used.
Figure 9:
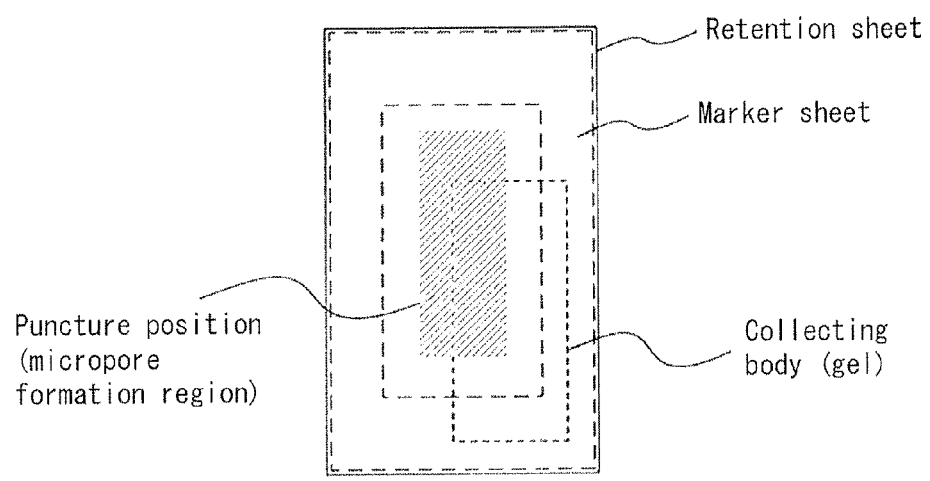

FIG. 7 is a perspective illustration diagram of a interstitial fluid collection sheet 10 that comprises: the retention sheet 11; and the collecting body 12 retained by this retention sheet 11. FIG. 8 is a cross-sectional diagram taken along the line B-B of FIG. 7.

The collecting body 12 is made of water-retentive gel that can retain interstitial fluid extracted from a subject skin and includes pure water as extraction medium. The gel may be any gel so long as the gel can collect interstitial fluid and can achieve the objective of the present invention. The gel is preferably formed of at least one type of hydrophilic polymer selected from the group consisting of polyvinyl alcohol and polyvinylpyrrolidone. The gel may be formed of hydrophilic polymer that may be polyvinyl alcohol only, polyvinylpyrrolidone only, or a mixture thereof. The gel is more preferably formed of hydrophilic polymer that is polyvinyl alcohol only or a mixture of polyvinyl alcohol and polyvinylpyrrolidone.

The gel can be formed by a method of cross-linking hydrophilic polymer in aqueous solution. The gel can be formed by coating aqueous solution of hydrophilic polymer on base material to form a coating film to thereby cross-link hydrophilic polymer included in the coating film. Cross-linking methods of hydrophilic polymer include chemical cross-linking and radiation cross-linking. However, radiation cross-linking is desirably used because this method suppresses gel from being mixed with impurities of various chemical substances.

In the present embodiment, the collecting body 12 has a rectangular parallelepiped shape, and a face thereof abuttable to the skin has a size of 7 mm×12 mm. This size is smaller than the size of the opening 3 of the marker sheet 2. Thus, the collecting body 12 can be placed within the opening 3 without protruding from the opening 3. This can consequently increase the area on which the collecting body 12 is abutted to the micropore formation region, thus efficiently collecting interstitial fluid extracted through the micropores. The collecting body 12 has a slightly larger size than that of a face of the fine needle chip in which fine needles are formed. This can consequently enable the use of the micropore formation region without waste to collect interstitial fluid, thus giving no excessive burden on the subject.

It is preferable that, in order to place the collecting body 12 within the opening 3 of the marker sheet 2 in an easy and accurate manner as in the marker sheet 2, the gel itself constituting the collecting body 12 is colored or a colored intermediate layer is used. The intermediate layer is used for the purpose of improving the anchoring property of the gel to the adhesive face and is directly placed on the surface of the pressure sensitive adhesive layer. The intermediate layer is preferably the one having a laminate structure of a nonwoven fabric of polyethylene terephthalate (PET) and a PET film or the one of a polyethylene film. The intermediate layer preferably has the same area as that of an area in which the gel is provided to the skin.

Figure 10:
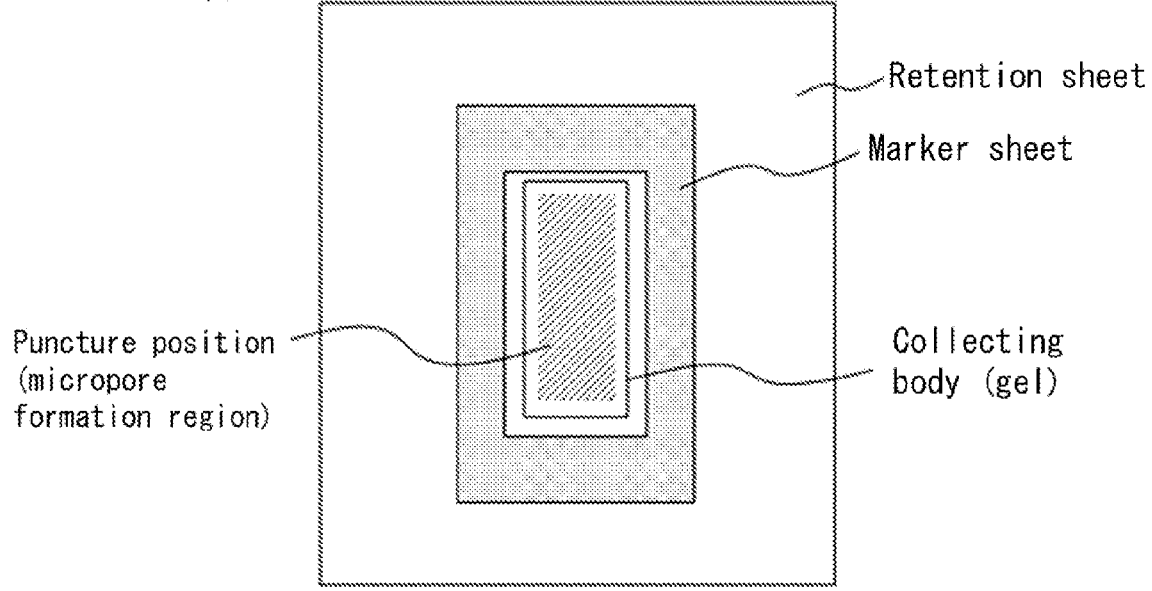
FIGS. 10(a) and 10(b) are illustration diagrams of a case where a transparent retention sheet is used.
Figure 10:
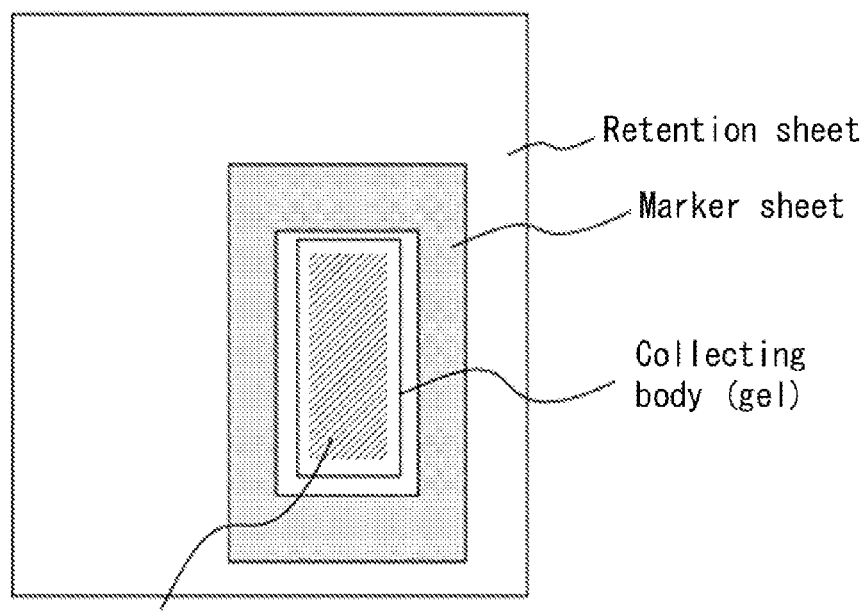

A retention sheet 11 is composed of: an oval-shaped sheet body 11a; and an pressure sensitive adhesive layer 11b formed on one face of the sheet body 11a. A face on which the pressure sensitive adhesive layer 11b is formed functions as an adhesive face. The collecting body 12 is provided at substantially the center of a similarly oval-shaped peeling sheet 13 that also functions as a mat board. The retention sheet 11 is adhered to the peeling sheet 13 so as to cover the collecting body 12. The collecting body 12 is retained to the retention sheet 11 by a part of the adhesive face of the retention sheet 11. In order to avoid the drying of the collecting body 12 during the collection of interstitial fluid, the retention sheet 11 has an area that can cover the collecting body 12. Specifically, by covering the collecting body 12 by the retention sheet 11, the space between the skin and the retention sheet 11 can be sealed in an air-tight manner during the collection of interstitial fluid. This can consequently restrain the water included in the collecting body 12 from evaporating during the collection of interstitial fluid. In the present embodiment, the retention sheet 11 has a larger area than the area of the marker sheet 2 so that the retention sheet 11 can sufficiently cover the collecting body 12 (see FIGS. 10(*a*) and 10(*b*)).

The sheet body 11a of the retention sheet 11 is colorless and transparent or colored and transparent. Thus, the collecting body 12 retained by the retention sheet 11 can be visually recognized easily at the surface-side of the sheet body 11a (an opposite face to the pressure sensitive adhesive layer 11b). The sheet body 11a is preferably made of material having a low moisture permeability in order to prevent the evaporation of interstitial fluid and the drying of the collecting body. Material having a low moisture permeability includes, for example, a polyethylene film, a polypropylene film, a polyester film, and a polyurethane film among which a polyethylene film and a polyester film are preferred. The thickness of the sheet body 11a is not particularly limited and is generally about 0.025 to 0.5 mm.

The interstitial fluid collection sheet 10 is adhered to the skin by the adhesive face of the retention sheet 11 so that the collecting body 12 is placed in the micropore formation region within the opening 3 of the marker sheet 2. During this process, since the retention sheet for retaining the collecting body 12 is transparent, the marker sheet 2 can be used as a marker to thereby easily place the collecting body 12 in the micropore formation region.

The collecting body 12 is retained by a part of the adhesive face of the retention sheet 11. Due to a manufacture reason, there may be a variation in the position of the collecting body 12 in the adhesive face. In such a case, the position at which the collecting body 12 is adhered undesirably varies if the interstitial fluid collection sheet 10 is adhered to a predetermined region of the skin based on the outer shape of the interstitial fluid collection sheet 10, which also may cause a lowered measurement accuracy. However, according to the present embodiment, since the retention sheet 11 is transparent, even when the position of the collecting body 12 in the retention sheet 11 varies, the interstitial fluid collection sheet 10 can be adhered to the skin, while visually recognizing the position of the collecting body 12, so that the collecting body 12 is positioned within the region defined by the marker sheet 2. This consequently allows, regardless of the variation of the position of the collecting body 12 in the retention sheet 11, the collecting body 12 to be placed in the micropore formation region.

The following section will describe an advantage of the interstitial fluid collection method according to the present embodiment with reference to the drawings. FIGS. 9(a) and 9(b) (Prior Art) are illustration diagrams in the case where an opaque retention sheet is used. FIG. 9(a) shows the collecting body retained at the center of the retention sheet. FIG. 9(b) shows the collecting body retained at a position dislocated to the right side of the center of the retention sheet. FIGS. 10(a) and 10(b) are illustration diagrams in the case where a transparent retention sheet is used. FIG. 10(a) shows the collecting body retained at the center of the retention sheet. FIG. 10(b) shows the collecting body retained at a position dislocated to the right side of the center of the retention sheet. In FIGS. 9(a) and 9(b) as well as FIGS. 10(a) and 10(b), those components that can be visually recognized are shown by the solid line while those components that cannot be visually recognized are shown by the broken line.

In FIGS. 9(a) and 9(b), a configuration will be exemplary described where the collecting body is retained at the center of the retention sheet having substantially the same size as that of the marker sheet and the outline of the marker sheet is aligned with the outline of the retention sheet. As shown in FIG. 9(a), when the collecting body is retained at the center of the retention sheet (i.e., when no variation is caused in the position of the collecting body), the collection body can be placed in the micropore formation region by aligning the retention sheet, even when the retention sheet is opaque, with the outline of the marker sheet without confirming the position of the collecting body. However, when the collecting body is retained at a position dislocated from the center of the retention sheet as shown in FIG. 9(b) (i.e., when a variation is caused in the position of the collecting body), the collecting body is not placed in the micropore formation region even when the retention sheet is adhered by aligning the outline of the marker sheet with the outline of the retention sheet. To prevent this, the retention sheet must be adhered while confirming the position of the collecting body. However, the position of the collecting body can not be visually recognized because of the opaque retention sheet, thus the collection body can not be accurately placed in the micropore formation region.

In contrast with this, in FIGS. 10(a) and 10(b), the existence of the transparent retention in accordance with the present inventive sheet allows the collecting body and the marker sheet to be visually recognized via the retention sheet as shown by the solid line. Thus, the collecting body can be accurately placed within the region defined by the marker sheet while visually confirming the position of the collecting body both in the case where the collecting body is retained at the center of the retention sheet as shown in FIG. 10(a) and the case where the collecting body is retained at a position dislocated from the center of the retention sheet as shown in FIG. 10(b). As described above, the use of the transparent retention sheet can allow the collecting body to be accurately placed in the micropore formation region, regardless of the variation of the position of the collecting body retained in the retention sheet.

In the configuration exemplarily shown in FIGS. 9(a) and 9(b), the retention sheet is opaque. Thus, in order to align the outline of the marker sheet with the outline of the retention sheet, the marker sheet must have substantially the same size as that of the retention sheet, thus failing to secure a sufficient area at which the retention sheet is adhered to the skin. When the retention sheet is transparent on the other hand, the size of the retention sheet to the marker sheet is not limited. Thus, the size of the retention sheet can be sufficiently increased to the marker sheet as shown in FIGS. 10(a) and 10(b). This consequently can increase the area at which the retention sheet is adhered to the skin, thus increasing the retention strength of the retention sheet for retaining the collecting body.

The adhesive face of the retention sheet 11 is adhered to the back face of the adhesive face of the marker sheet 2 with a lower adhesive strength than the adhesive strength by the marker sheet 2 to the skin. This prevents, when the retention sheet 11 is peeled from the skin after the collection of interstitial fluid, the marker sheet 2 from being peeled from the skin together with the retention sheet 11. This can consequently prevent the components of the horny layer attached to the marker sheet 2 from being measured together with the interstitial fluid collected in the collecting body 12, thus improving a measurement accuracy. An adhesive strength by the pressure sensitive adhesive layer 11b of the retention sheet 11 can be adjusted as in the adjustment of the adhesive strengths of the pressure sensitive adhesive layers of the marker sheet 2 and the marker retention sheet 1. The pressure sensitive adhesive layer may be formed by pressure sensitive adhesive including, for example, acrylic pressure sensitive adhesive, rubber-base pressure sensitive adhesive, silicone-base pressure sensitive adhesive, and urethane-base pressure sensitive adhesive. The interstitial fluid collection sheet 10 of the present embodiment is frequently adhered to the skin surface for a relatively long time. Thus, these pressure sensitive adhesives are preferably restrained from causing skin irritation. From the viewpoint of restraining skin irritation, acrylic pressure sensitive adhesive and rubber-base pressure sensitive adhesive are preferred and acrylic pressure sensitive adhesive is more preferred.

[Interstitial Fluid Collection Method]

Next, the following section will describe a interstitial fluid collection method using the above-described interstitial fluid collection kit.

Figure 11:
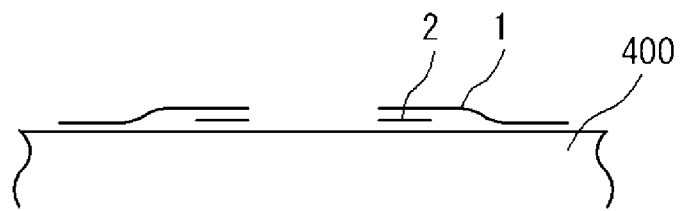
FIGS. 11(a)-11(e) illustrate steps of the interstitial fluid collection method.
Figure 11:
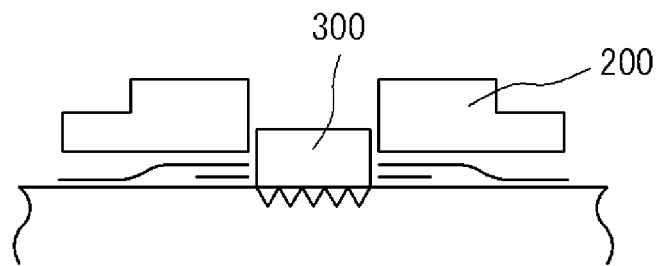
Figure 11:
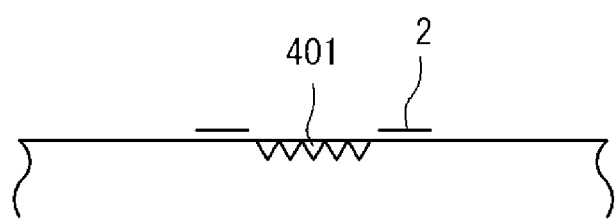
Figure 11:
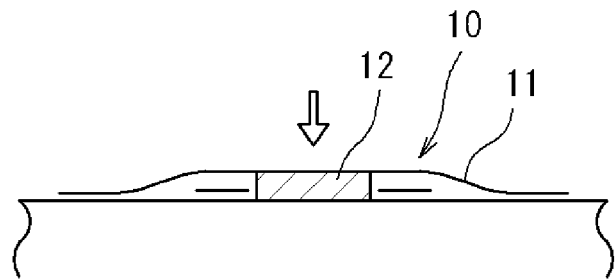
Figure 11:
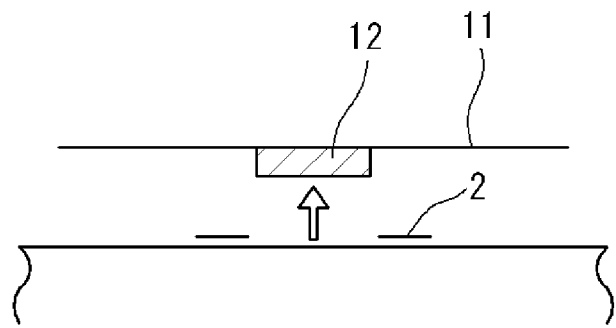

FIG. 11 is a diagram illustrating steps of the interstitial fluid collection method using the above-described interstitial fluid collection kit. First, the skin 400 of a subject is cleaned by alcohol for example to remove substances (e.g., sweat, dust) that may disturb a measurement result. Thereafter, the marker sheet 2 retained by the marker retention sheet 1 is adhered to a predetermined position of the skin of the subject (step (a)).

Next, micropores are formed in the skin by the puncture tool 200 attached with the fine needle chip 300 (step (b)). Specifically, the position of the puncture tool 200 is set by aligning the notches 206 formed in the flange 205 at the lower end of the puncture tool 200 with the notches 6 of the marker retention sheet 1. This consequently provides the alignment between the opening formed in the lower end face of the lower section 201a of the housing 201 and the opening 3 of the marker sheet 2. When the release button 202 is depressed in this status, the fixing of the array chuck 203 by the fixing mechanism is released and the array chuck 203 is moved to the skin side by the biasing force of the spring member 204. Then, the fine needle chip 300 attached to the lower end of the array chuck 203 passes through the opening formed in the lower end face of the lower section 201a of the housing 201 and is abutted to the skin region of the subject defined by the marker sheet 2. As a result, the micropores 401 are formed in the epidermis of the subject skin.

Next, the puncture tool 200 is removed from the subject skin and the marker retention sheet 1 is peeled from the subject skin (step (c)). As described above, the adhesive face of the marker retention sheet 1 has an adhesive strength lower than the adhesive strength of the adhesive face of the marker sheet 2. Thus, the marker sheet 2 is prevented from being peeled together with the marker retention sheet 1, thus allowing the marker sheet 2 to be continuously adhered to the subject skin.

Next, the interstitial fluid collection sheet 10 is adhered to the subject skin using the marker sheet 2 as a marker so that the collecting body 12 is placed within the opening 3 of the marker sheet 2 (step (d)). In this case, since the retention sheet 11 in the present embodiment is transparent, the interstitial fluid collection sheet 10 can be adhered to the skin, while the position of the collecting body 12 being visually confirmed, so that the collecting body 12 is positioned within the region defined by the marker sheet 2.

By leaving the collecting body 12 placed in the micropore formation region for a predetermined time of 60 minutes or more and preferably 180 minutes or more for example, interstitial fluid extracted through the micropores is collected in the collecting body 12 (step (d)). In the present embodiment, since the retention sheet for retaining the collecting body is adhered to the skin, there is no need to attach an aid such as a belt to the arm, even when interstitial fluid is collected for a long time of 60 minutes to 180 minutes, thus reducing the burden to the user.

After the predetermined time after the placement of the collecting body 12 in the micropore formation region, the interstitial fluid collection sheet 10 is peeled from the subject skin (step (e)). During this process, since the adhesive face of the retention sheet 11 is adhered to the back face of the adhesive face of the marker sheet 2 with a lower adhesive strength than the adhesive strength of the marker sheet 2 to the skin, the marker sheet 2 is prevented from being peeled from the skin together with the retention sheet 11.

Figure 12:
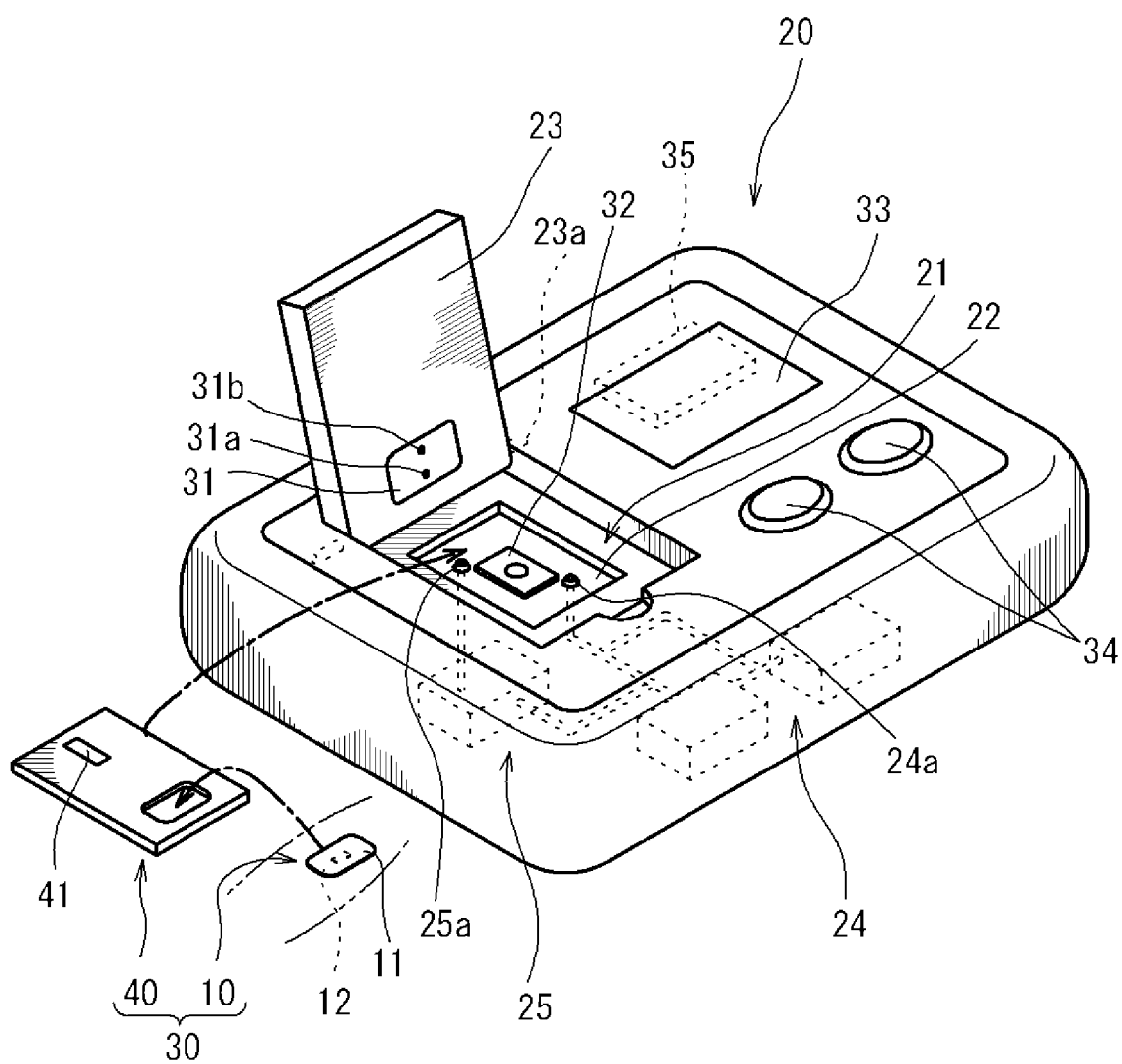
FIG. 12 is a perspective illustration diagram illustrating an appearance of a living body component analyzer.

The interstitial fluid collected in the collecting body 12 is subjected to an analysis of components by an analyzer shown in FIG. 12 for example.

FIG. 12 is a perspective illustration diagram illustrating the appearance of a living body component analyzer. The living body component analyzer 20 is used to acquire a glucose concentration and a sodium ion concentration included in the interstitial fluid collected in the collecting body 12. The living body component analyzer 20 is used in the manner as described below. First, as shown by the dashed line in FIG. 12, the interstitial fluid collection sheet 10 removed from the subject skin is adhered to an analysis cartridge 40. Then, this analysis cartridge 40 is placed in a cartridge receiving section 22 of the living body component analyzer 20. Then, the living body component analyzer 20 carries out a predetermined analysis processing on the analysis cartridge 40 placed in the cartridge receiving portion 22 and the interstitial fluid collection sheet 10 adhered to the analysis cartridge 40 to thereby acquire a glucose concentration and a sodium ion concentration of the interstitial fluid collected in the interstitial fluid collection sheet 10.

The living body component analyzer 20 includes a thick rectangular parallelepiped-shaped housing. A top panel in the upper face of the housing includes a concave portion 21. The concave portion 21 includes the cartridge receiving portion 22 that is a concave portion more deeply formed than the concave portion 21. The concave portion 21 is also connected to a movable top panel 23 that has substantially the same thickness as the height of a side wall of the concave portion 21. The movable top panel 23 in the status shown in FIG. 12 can be stored in the concave portion 21 by being folded down around a pivot axis 23a. The movable top panel 23 stored in the concave portion 21 also can be raised as shown in FIG. 12. The cartridge receiving portion 22 is sized so as to be able to accommodate the analysis cartridge 40 which will be described later.

The movable top panel 23 is supported by the pivot axis so as to be biased in a direction along which the movable top panel 23 is stored in the concave portion 21. Thus, the analysis cartridge 40 placed in the cartridge receiving portion 22 is pushed down from the upper side by the movable top panel 23.

The living body component analyzer 20 includes therein a solution sending section 24 and a liquid discharge section 25. The solution sending section 24 is a mechanism to send liquid to the analysis cartridge 40 placed in the cartridge receiving portion 22. The solution sending section 24 sends liquid via a nipple 24a to the analysis cartridge 40 placed in the cartridge receiving portion 22. The liquid discharge section 25 is a mechanism to discharge liquid sent from the solution sending section 24 to the analysis cartridge 40. The liquid discharge section 25 discharges, via a nipple 25a, the liquid sent to the analysis cartridge 40.

The living body component analyzer 20 further comprises: a glucose detection section 31; a sodium ion detection section 32; a display section 33; an operation section 34; and a control section 35.

The glucose detection section 31 is provided in the back face of the movable top panel 23 (i.e., a face opposed to the cartridge receiving portion 22 when the movable top panel 23 is stored in the concave portion 21). The glucose detection section 31 comprises a light source 31a for emitting light and a light-receiving section 31b for receiving reflected light of light emitted from this light source 31a. Thus, the glucose detection section 31 is configured to emit light to the analysis cartridge 40 placed in the cartridge receiving portion 22 and to receive the reflected light from the analysis cartridge 40 having received the light. The analysis cartridge 40 includes a glucose reactant 41 that can react chemically with the glucose in the interstitial fluid collected from the living body to change the color thereof. The glucose detection section 31 can detect the change in absorbance due to glucose as described above based on the reflected light and can determine the quantity of glucose based on the resultant reflected light.

The sodium ion detection section 32 is provided in the bottom face of the cartridge receiving portion 22. The sodium ion detection section 32 includes a rectangular plate-like member provided in the bottom face of the cartridge receiving portion 22. At substantially the center of the plate-like member, a pair of sodium ion concentration measurement electrodes is provided. The sodium ion concentration measurement electrodes include a sodium ion-selective electrode that includes a sodium ion selective film and that is made of silver/silver chloride and a counter electrode of a silver/silver chloride electrode.

The control section 35 is provided in the living body component analyzer 20 and comprises a CPU, a ROM, and a RAM for example. The CPU reads and executes a program stored in the ROM to thereby control the operations of the respective sections. The RAM is used as a program development region when a program stored in the ROM is executed.

Next, the following section will describe the operation of the living body component analyzer 20 having the configuration as described above.

The interstitial fluid collection sheet 10 for which the interstitial fluid collection is completed is stored in a storage portion of the analysis cartridge 40. Next, the analysis cartridge 40 is placed in the cartridge receiving portion 22.

Upon receiving an instruction for executing the measurement, the solution sending section 24 sends liquid via the nipple 24a to the storage portion of the analysis cartridge 40 and the storage portion is filled with the liquid. Then, the living body component analyzer 20 in this status is left for a predetermined time, thus allowing the components in the interstitial fluid to be diffused from the collecting body 12 to the liquid. As described above, when the retention sheet 11 is peeled from the skin, the marker sheet 2 is prevented from being peeled from the skin together with the retention sheet 11. This consequently prevents the horny layer components attached to the marker sheet 2 from dissolving in the liquid, thus preventing the horny layer components from having an influence on the measurement accuracy.

After passage of the predetermined time, the solution sending section 24 sends air to the storage portion. By the air sent from the solution sending section 24, the liquid filled in the storage portion is sent to a flow path provided in the lower face of the analysis cartridge 40 and is further sent via the flow path to the glucose reactant 41. The liquid sent to the flow path contacts with the sodium ion detection section 32. The liquid sent to the glucose reactant 41 reacts with the glucose reactant 41 to thereby change the color of the glucose reactant.

The control section 35 applies a fixed voltage to the sodium ion concentration measurement electrode to acquire a current value. Based on the acquired current value and a calibration curve stored in the control section 35 in advance, the control section 35 acquires the sodium ion concentration.

The control section 35 acquires glucose concentration based on a change amount between the received light amount of the light-receiving section 31b prior to the color formation of a color forming dye and the received light amount of the light-receiving section 31b after the color formation of the color forming dye.

Other Modification Examples

The present invention is not limited to the above-described embodiments and can be subjected to various modifications.

For example, in the above-described embodiment, the marker sheet is retained by the marker retention sheet and the marker retention sheet is used to adhere the marker sheet to the skin. However, the marker retention sheet as described above can be omitted.

Figure 13:
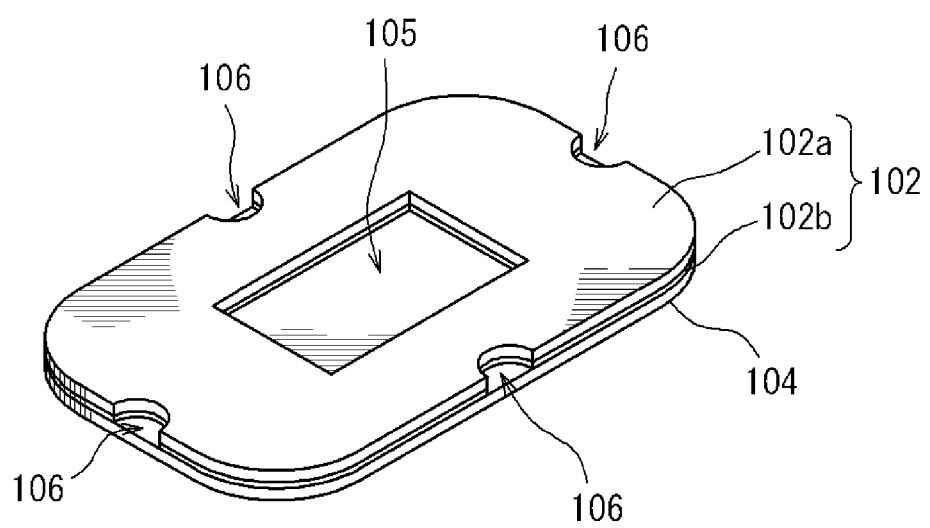
FIG. 13 is a perspective illustration diagram of another example of the marker sheet.

FIG. 13 is a perspective illustration diagram of a marker sheet 102 as described above. This marker sheet 102 has an oval shape and is composed of a sheet body 102a and an pressure sensitive adhesive layer 102b. The marker sheet 102 is adhered to a peeling sheet 104 and includes an opening 105 at the center thereof. Peripheries opposed to one another to sandwich the opening 105 have four notches 106 each of which has shape corresponding to each of the notches formed in the flange of the puncture tool.

The marker sheet 102 is adhered to the subject skin after the peeling sheet 104 is peeled. Then, the notches 106 and the notches formed in the flange are used to position the puncture tool. Then, the puncture tool is used to form micropores in the opening 105.

After the formation of the micropores, a interstitial fluid collection sheet is adhered to the subject skin so that the collecting body of the interstitial fluid collection sheet is positioned within the opening 105. After the extraction of interstitial fluid, the interstitial fluid collection sheet is peeled from the skin and the above-described measurement is carried out.

Figure 14:
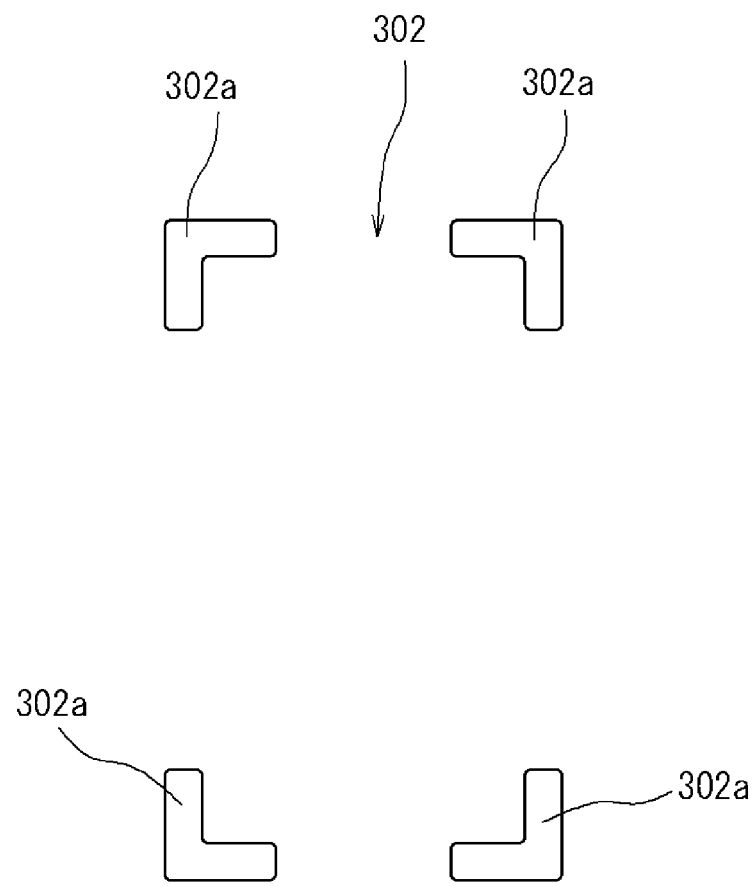
FIG. 14 is a top view of another example of the marker sheet.
Figure 15:
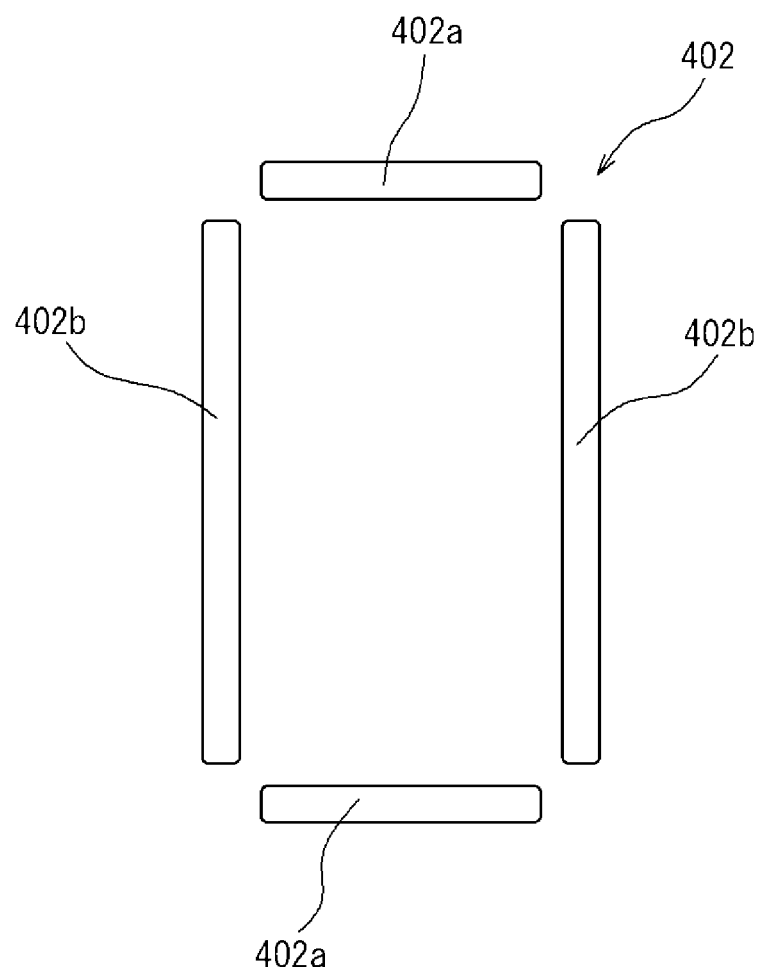
FIG. 15 is a top view illustrating another example of the marker sheet.

The marker sheet is not limited to a single sheet. The marker sheet can be composed of a plurality of small pieces so long as the marker sheet can define a region in which micropores are formed and can function as a marker for placing the collecting body. FIG. 14 illustrates a marker sheet 302 composed of four small pieces 302a each of which has a substantially L-like shape. FIG. 15 illustrates a marker sheet 402 composed of two short strips 402a and two long strips 402b. In the case of the marker sheets shown in FIG. 14 and FIG. 15, it is troublesome to accurately adhere each small piece to the skin and it is also difficult to adhere each small piece to a predetermined position. Thus, it is preferable that the marker sheet composed of a plurality of small pieces is retained by a marker retention sheet and this marker retention sheet is adhered to the predetermined position of the skin and the marker retention sheet is peeled after the puncture.

Another modification example is also possible where the back face of the marker sheet is surrounded by an pressure sensitive adhesive layer so that the formation of micropores in the skin is performed substantially simultaneously with the adhesion of the marker sheet to the skin. Specifically, while the shape of the flange of the puncture tool is being aligned with the notches of the marker sheet, the pressure sensitive adhesive formed on the back face of the marker sheet is adhered to the flange.

The notch as a positioning mark is not limited to a semicircular shape and also can appropriately have other shapes such as a triangular or rectangular shape. When a plurality of notches are used, notches having different shapes to one another can be used. In this case, the flange of the puncture tool also includes notches having corresponding different shapes to one another. This can provide the positioning of the puncture tool easily when the opening through which the fine needle chip passes is not provided at the center of a face of the puncture tool that is abutted to the skin. The number of the notches is preferably two or more and is particularly preferably four. In this case, each of the four cutouts is preferably provided at substantially the center of each side of two sides symmetric to each other.

Another modification example of the positioning mark is also possible where the positioning mark has a convex shape corresponding to a hole made in the flange of the puncture tool. Other modification examples also include a positioning mark additionally prepared as an adhesive tape that is adhered to the marker sheet.

Although the present embodiment has shown an example in which gel is used as the collecting body, the collecting body is not limited to gel and may be any water-absorbing material including mesh and paper for example so long as the material can collect extracted interstitial fluid.

The invention claimed is:

1. A method of adhering a collecting body for collecting interstitial fluid, including:
   a step of adhering, to skin, a marker sheet that has a first adhesive face with a first adhesive and that defines a region in which micropores are to be formed,
   a step of releasing adhesion between the marker sheet and a marker retention sheet that has a second adhesive face adhered to a back face of the marker sheet by a second adhesive having a strength lower than a strength of the first adhesive;
   a step of adhering to the skin by an adhesive face of a transparent retention sheet, by using the marker sheet adhered to the skin as a marker so that the collecting body is placed on the region, an interstitial fluid collection sheet which includes the transparent retention sheet having an adhesive face and the collecting body that is retained by a part of the adhesive face of the retention sheet and that is capable of collecting extracted interstitial fluid extracted from the skin,
   wherein the marker sheet has a smaller size than that of the marker retention sheet;
   wherein the marker sheet frames an opening that defines the region in which micropores are to be formed; and
   wherein the marker retention sheet has an opening that is aligned with the opening of the marker sheet.

2. An interstitial fluid collection kit for collecting interstitial fluid extracted via micropores formed in a skin, comprising:
   a marker sheet that has a first adhesive face with a first adhesive and that defines a region in which micropores are to be formed;
   second adhesive face adhered to a back face of the marker sheet by a second adhesive having a strength lower than a strength of the first adhesive,
   a transparent retention sheet having an adhesive face; and
   a collection body that is retained by a part of the adhesive face of the transparent retention sheet and that is capable of collecting extracted interstitial fluid extracted from the skin,
   wherein the marker sheet has a smaller size than that of the marker retention sheet;
   wherein the marker sheet frames an opening that defines the region in which micropores are to be formed; and
   wherein the marker retention sheet has an opening that is aligned with the opening of the marker sheet.

3. The interstitial fluid collection kit according to claim 2, wherein the marker sheet consists of a plurality of pieces by which the region is defined.

4. The interstitial fluid collection kit according to claim 2, wherein the collecting body is gel.

5. The interstitial fluid collection kit according to claim 4, wherein the gel is colored, or the interstitial fluid collection kit has a colored intermediate layer positioned between the retention sheet and the collecting body.

6. The interstitial fluid collection kit according to claim 2, wherein the collecting body is smaller than the opening of the marker sheet.

7. The interstitial fluid collection kit according to claim 2, wherein the marker sheet is colored.

8. The interstitial fluid collection kit according to claim 2, wherein the marker sheet has a positioning mark that corresponds to a positioning mark provided on a flange provided on a side of a micropore formation tool, the side being abuttable to the skin.

9. The interstitial fluid collection kit according to claim 2, wherein the marker retention sheet has a positioning marker that corresponds to a positioning mark provided on a flange provided on a side of a micropore formation tool, the side being abuttable to the skin.

10. The interstitial fluid collection kit according to claim 2, wherein the marker sheet has a positioning mark comprising a notch that corresponds to a positioning mark provided on a flange on a side of a micropore formation tool, the side being abuttable to the skin, and the positioning mark of the marker sheet being on a plurality of sides of the marker sheet.

* * * * *